United States Patent [19]
Hinzpeter et al.

[11] Patent Number: 5,455,157
[45] Date of Patent: Oct. 3, 1995

[54] METHOD FOR THE NON-RADIOACTIVE MEASUREMENT OF THE NUCLEIC ACID SYNTHESIS IN EUKARYOTIC CELLS

[75] Inventors: Matthias Hinzpeter, München; Herbert von der Eltz, Weilheim, both of Germany

[73] Assignee: Boehringer Mannheim GmbH, Mannheim-Waldhof, Germany

[21] Appl. No.: 231,364

[22] Filed: Apr. 19, 1994

Related U.S. Application Data

[63] Continuation of Ser. No. 754,359, Aug. 29, 1991, abandoned, which is a continuation of Ser. No. 527,080, May 22, 1990, abandoned.

[30] Foreign Application Priority Data

May 22, 1989 [DE] Germany ................ 39 16 595.7

[51] Int. Cl.⁶ .................... C12Q 1/68; G01N 33/53; C07H 21/04; C07H 21/02
[52] U.S. Cl. .................... 435/6; 435/7.1; 436/63; 436/94; 436/501; 436/829; 436/23.1; 935/76; 935/77; 935/78; 264/4.1; 264/4.3
[58] Field of Search .................... 435/6, 7.1; 436/63, 436/94, 501, 829; 935/76, 77, 78; 264/4.1, 4.3; 536/23.1

[56] References Cited

U.S. PATENT DOCUMENTS

| | | | |
|---|---|---|---|
| 4,515,736 | 5/1985 | Deamer | 264/4.3 |
| 4,585,736 | 4/1986 | Dolbeare et al. | 435/6 |
| 4,711,955 | 12/1987 | Ward et al. | 536/29 |

FOREIGN PATENT DOCUMENTS

| | | |
|---|---|---|
| 0063879 | 11/1982 | European Pat. Off. . |
| 0172007 | 2/1986 | European Pat. Off. . |
| 0173251 | 3/1986 | European Pat. Off. . |
| WOA8902733 | 4/1989 | WIPO . |

OTHER PUBLICATIONS

Porstmann et al., J. Immunol. Meth., 82: 169–179 (1985).
Felgner et al., Proc. Natl. Acad. Sci. 84: 7413–7417 (Nov. 1987).
Stamatatos et al., Biochem. 27: 3917–3925 (1988).

Primary Examiner—Mindy B. Fleisher
Assistant Examiner—Ching-I Patsy Lin
Attorney, Agent, or Firm—Felfe & Lynch

[57] ABSTRACT

For the determination of the rate of nucleic acid synthesis in eukaryotic cells a nucleotide which is non-radioactively labelled or derivatized with a hapten is introduced into the cells with the addition of liposomes and the rate of synthesis of the nucleic acids is determined by means of the incorporation of the nucleotide via its label or derivatization.

18 Claims, No Drawings

METHOD FOR THE NON-RADIOACTIVE MEASUREMENT OF THE NUCLEIC ACID SYNTHESIS IN EUKARYOTIC CELLS

This application is a continuation, of application Ser. No. 07/754,359, filed Aug. 29, 1991, now abandoned which is a continuation of application Ser. No. 07/527,080, filed May 22, 1990, now abandoned.

Description

The invention concerns a method for the determination of the rate of nucleic acid synthesis of eukaryotic cells.

For the determination of the rate of nucleic acid synthesis and hence of the proliferation of eukaryotic cells, radioactively labelled nucleosides ($^3$H, $^{32}$p, $^{14}$C etc) which are taken up by the cells in vivo, phosphorylated and incorporated into the cellular nucleic acid as nucleic acid building blocks have been mainly used up to now (B. Helpap and W. Maurer Naturwissenschaften 54 (1967), 520). The radioactivity incorporated in the cellular nucleic acid can then be determined using a counter or other known techniques.

There is a general tendency to replace the handling of radioactive materials by the use of non-radioactive labels. The reasons for this are based inter alia on the known risks in the use of radioactive materials. However, well-known non-radioactive labels such as e.g. fluorescent dyes or enzyme labels are usually molecules of considerable size and cannot be easily introduced into living cells. It was therefore suggested by H. G. Gratzner et al., Exp. Cell Res. 95 (1975), 88; and H. G. Gratzner et al., J. Histochem. Cytochem. 24, (1976), 34, that the nucleoside 5-bromo-2-deoxyuridine be introduced into the cells instead of radioactively labelled nucleosides (such nucleosides are taken up by the cells without auxiliary agents in the same way as the radioactively labelled nucleosides). The incorporation of this nucleoside was then detected by means of a specific antibody directed against it which is likewise provided with a label. Studies have been published which describe the quantification of the incorporation of 5-bromo-2-deoxyuridine into the cellular DNA by means of an enzyme-immunoassay (T. Porstmann et al., J. Immunol. Methods 83 (1985), 169–179; F. Martinon et al., Lab. 23 (1987), 153–159). However, in order to detect the 5-bromo-2-deoxyuridine incorporated into the cellular DNA, the cellular DNA has to be denatured. Such a drastic treatment of the cells leads to a relatively high "background" in a cell ELISA carried out subsequently and as a result the determination of the rate of synthesis is made more difficult and inaccurate. As has now been found, a substitution of the bromine derivative by a nucleoside labelled with a hapten results in no incorporation of it into the nucleic acid so that the determination of the hapten which can be carried out without drastic treatment of the cells could not be used.

It is therefore the object of the present invention to provide a method which allows a simple and accurate detection of the rate of nucleic acid synthesis of eukaryotic cells in which, however, the use of radioactive compounds and a denaturation of the cells should be avoided.

This object is achieved according to the present invention by a method for the determination of the rate of nucleic acid synthesis which is characterized in that a nucleotide which is non-radioactively labelled or derivatized with a hapten is introduced into the cells via liposomes and the rate of synthesis of the nucleic acids is determined by means of the incorporation of the nucleotide via its label or derivatization.

The invention is based on the surprising fact that when using labelled nucleotides, in contrast to the use of labelled nucleosides, using liposomes, the desired incorporation into the nucleic acids takes place and can be used as a measure for the rate of nucleic acid synthesis.

By use of the method according to the present invention it is possible to incorporate a nucleotide molecule into the newly synthesized nucleic acid (DNA/RNA) in cells and subsequently to determine it by means of its label. The labelling is preferably by a fluorescent dye or by a derivatization which is in turn detectable. The rate of nucleic acid synthesis in the cells can therefore be determined by the rate of incorporation of the labelled or derivatized nucleotide. Nucleotides occurring naturally or other nucleotides of the ribo-, deoxy- and dideoxynucleotide series can be used as the nucleotides.

All non-radioactive labels can be used according to the present invention as labels.

In the preferred use of a nucleotide labelled with a hapten its determination is preferably carried out via a likewise labelled anti-hapten antibody. All haptens are suitable as haptens which do not hinder the incorporation of the nucleotide into the nucleic acid by their excessive size or which do not hinder the rate of nucleic acid synthesis and which can be detected by a specific anti-hapten antibody. Molecules with a molecular weight of 300–1200 are preferably used as the hapten such as steroids and compounds similar to steroids (such as e.g. cortisol, oestriol, oestradiol, theophylline, testosterol, bile acids, progesterone, aldosterone, digoxin, digoxigenin, scillarenin, bufataline, ecdysone and tomatidine); short-chain peptides (such as antipressin, oxytocin and bradykinin); fluorescent dyes (such as e.g. fluorescein and its derivatives, resorufin, rhodamine etc); $T_3$, $T_4$, biotin and its derivatives; aflatoxin, atrazine; plant hormones (such as e.g. gibberillins); alkaloids (such as e.g. reserpine and ajamalicine); phenobarbitals; vitamins (such as e.g. B 12 and its derivatives). Digoxigenin, biotin or fluorescein are preferably used as haptens according to the present invention. Monoclonal or polyclonal antibodies or their fragments and derivatives can be used as anti-hapten antibodies. Such antibodies are known to the expert.

Instead of an anti-hapten antibody another partner of a binding system which includes the hapten as the binding partner, which in turn can carry a detectable label, can also be used for the hapten test. Streptavidin or avidin are, for example, suitable as partners in such a binding system with biotin as the hapten, however, other molecules of comparable size which together form a binding pair are also suitable.

Nucleotides which are preferably used according to the present invention are pyrimidine nucleotides labelled or derivatized at the 5-position, purine nucleotides labelled or derivatized at the 8-position or 7-deazapurine nucleotides labelled or derivatized at the 7-position, with ribose, deoxyribose or dideoxyribose as the sugar residue in each case; particularly preferred is 5-digoxigenin-2-deoxyuridine triphosphate which is detected by a high affinity monoclonal antibody directed towards digoxigenin. A Fab fragment of a polyclonal antibody is particularly preferably used.

A fluorescent dye is preferably used for the non-radioactive labelling of the nucleotide as well as of the anti-hapten antibody or of the labelled partner of a binding system. Suitable fluorescent dyes are known to the expert: resorufin, rhodamine, coumarin or fluorescein are preferably used according to the present invention. In another preferred embodiment an enzyme label is used as the label of the nucleotide, of the anti-hapten antibody or of the other partner of the binding pair and the determination of the rate of incorporation is carried out via cleavage of a substrate by the enzyme label. In this case the rate of incorporation of the modified nucleotide and hence the rate of the nucleic acid synthesis can be derived from the enzymatic activity. Enzymes known to the expert are again suitable as enzyme labels. β-galactosidase, alkaline phosphatase or peroxidase are preferably used. The enzyme label is used particularly preferred as the label of the anti-hapten antibody or of the other partner of the binding system.

Liposomes which can permeate cell membranes, natural and synthetic liposomes as they are known to the expert are in general suitable as liposomes within the scope of the invention. Particularly suitable are cationic liposomes such as those mentioned in the general formula I in EP-A-01 72 007. EP 01 72 007 teaches that liposomes may be prepared from any compound having the requisite hydrophilic and hydrophobic activity. Many lipids have been developed for making liposomes wherein the hydrophilic group is phosphate, carboxylate, sulfate, amino, hydroxyl or a choline group, and the lipophilic group is alkyl, alkenyl, polyoxyalkenyl or alkyl substituted with aromatic or cycloalkyl, for example, ternary and complex lipids, glycerides, cerides, etholides and sterides.

Liposomes may be anionic, cationic or neutral depending upon the choice of hydrophilic group. For instance, when a compound with a phosphate or a sulfate group is used, the resulting liposomes will be anionic. When amino-containing lipids are used, the liposomes will have a positive charge, and will be cationic liposomes. When polyethylenoxy or glycol groups are present in the lipid, neutral liposomes are obtained. Additional compounds suitable for forming liposomes may be found in *McCutchen's Detergents and Emulsifiers* and *McCutchen's functional materials,* Allured Publishing Company, Richwood, N.J., U.S.A.

Preferred lipids are phospholipid-related materials, such as lecithin, phosphatidylethanolamine, lysolethicin, lysophosphatidylethanolamine, phosphatidylserine, phosphatidylinositol, sphingomyelin, cephalin, cardiolipin, phosphatidic acid, cerebrosides, dicetylphosphate, Additional non-phosphorous containing lipids are, e.g., stearylamine, dodecylamine, hexadecylamine, acetyl palmitate, glycerol ricinoleate, hexadecyl stereate, isopropyl myristate, amphoteric acrylic polymers, triethanolamine-lauryl sulfate, alkylaryl sulfate polyethyloxylated fatty acid amides, and the like. Particularly preferred non-phosphorous containing lipids have the formula I:

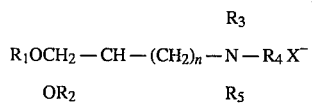

wherein $R_1$ and $R_2$ are independently alkyl or alkenyl of 6–22 carbons; $R_3$, $R_4$ and $R_5$ are each independently hydro, alkyl of 1–8 carbons, aryl or arylalkyl of 7–11 carbons; n is an integer of from 1–8; and X is a pharmaceutically acceptable anion. Further suitable cationic liposomes are described in the literature references JACS 99 (1977), 3860 and Biophysical Chemistry 10 (1979), 261.

For example, didodecyldimethylammonium bromide (Eastman) is recrystallized twice from ethyl acetate, mp 55°–56° C. and suspended in deionized water. A clear solution (10 mM) is obtained by sonication for four hours at 50° C. A few drops of this solution is applied to a 150 mesh copper grid coated with a carbon film which was then dried in a desiccator. A 2% aqueous solution of uranyl acetate was applied in a similar way. Spheric objects of 300–500 angstroms can clearly be seen on an electron micrograph.

The same aqueous solution of didodecylmethyl ammonium bromide was mixed with an equal amount of uranyl acetate solution, sonicated for 10–15 minutes and applied to a copper grid. Under electron microscopy, the multilayered vesicles, having a diameter of 1000 to 2000 angstroms, which contain uranyl acetate in the interior are visible. The thickness of the layer is about 40 angstroms both in the lamellar structure and in the multi-layered vesicle.

It is preferred to use liposomes according to EP-A-01 72 007 in combination with phospholipids such as e.g. dioleylphosphatidyl ethanolamine (PtdEtn) or dioleylphosphatidyl choline. A phospholipid in an amount of up to 75%, particularly preferably in a maximum amount of 50% is preferably added to the lipid. It is, however, especially preferred to use lipids free of phosphate.

Liposomes are prepared, for example, by suspending the lipids in water and treating them until a clear solution is obtained, for example, by means of ultrasonication or by pressing through small jets. Further details relating to suitable liposomes according to the present invention are found e.g. in Gregory Gregoriadis (1984) Preparation of Liposomes, Liposome Technology, Vol. 1, C.R.C. Press, Boca Raton, Fla.

Liposomes formed from N-[1-(1,2-dioleyloxy)propyl]-N,N,N-trimethylammonium chloride are preferably used. The use of these DOTMA liposomes for the transfection of DNA into eukaryotic cells has been described by P. L. Felgner et al., Proc. Natl. Acad. Sci. USA 84, (1987) 7413–7417.

A growth medium containing serum is preferably used for the introduction of the liposomes into the cells.

The determination of the rate of synthesis via the labelling of the nucleotide, of the anti-hapten antibody or of the other partner of the binding system is preferably carried out via the immunofluorescence of the proliferating cells when using a fluorescent dye or the fluorescence is measured directly.

In other preferred embodiments of the invention an immunocytochemical examination of the proliferating cells is used for the determination or a cell ELISA (enzyme-linked immunosorbent assay) is carried out. By this means it is possible in a simple and practicable manner to carry out a very accurate determination of the rate of nucleic acid synthesis in the cells in which the results are not falsified by a high background caused by the denaturation of the cellular nucleic acid.

By means of liposomes composed of cationic detergents combinations of non-radioactively labelled nucleotides with other non-labelled substances, such as e.g. inositol phosphates, DNA and RNA, therapeutic agents, hormones such as e.g. oestrogens, can also be introduced into eukaryotic cells for the purpose of measuring the nucleic acid synthesis which is specific for the unlabelled substances introduced.

The nucleic acid synthesis induced by inositol triphosphate can be measured according to the described procedures using a combination of labelled nucleotide with e.g. unlabelled inositol triphosphate.

Using a combination of labelled deoxyribonucleotide and unlabelled DNA, e.g. plasmid DNA, the replicative nucleic acid synthesis of this plasmid can be detected by e.g. transferring the unlabelled plasmid onto a membrane by means of a Southern blot and then hybridizing against the labelled newly synthesized (replicated) plasmid DNA. The transcriptive nucleic acid synthesis can be detected with a combination of labelled ribonucleotide and unlabelled mRNA by e.g. transferring the unlabelled mRNA onto a membrane by means of a Northern blot and then hybridizing against the labelled newly synthesized (transcribed) mRNA.

Using a combination of labelled ribonucleotide and unlabelled DNA, e.g. plasmid DNA, the transcriptive nucleic acid synthesis of this plasmid can be detected by e.g. transferring the unlabelled plasmid onto a membrane by means of a Southern blot and then hybridizing against the labelled newly synthesized (transcribed) mRNA. The reverse transcriptive nucleic acid synthesis can be detected, e.g. in cells infected with HIV, using a combination of labelled deoxyribonucleotide and unlabelled RNA by e.g. transferring the unlabelled RNA onto a membrane by means of a Northern blot and then hybridizing against the labelled newly synthesized (reversely transcribed) DNA. A combination of labelled deoxyribonucleotide and dideoxynucleotides can be used in the same way.

The following Examples elucidate the invention.

EXAMPLE 1

Preparation of the liposomes

Preparation of DOTMA {-[1-(2,3,-dioleyloxy)propyl]-N, N,Ntrimethylammonium chloride}

DOTMA may be prepared according to the following protocol: A mixture of 3-(dimethylamino)-1,2-propanediol (Aldrich; 1.19 g, 10 mmol), potassium tert-butoxide (3.36 g, 30 mmol), and oleyl ptoluenesulfonate (12.7 g, 30 mmol) in xylene (50 ml) was stirred at room temperature and reduced pressure (30 torr; 1 torr=133 Pa) for 30 min and then was heated to 50° C. with stirring for an additional 15 min. The reaction vessel was purged with nitrogen, and the mixture was heated to reflux ($\approx$140° C.) for 3 hr. After cooling, the reaction mixture was diluted with hexane (100 ml), and the resulting solution was extracted with water (twice, 50 ml each). The organic layer was concentrated, and the residue was chromatographed over silica gel by elution with a mixture of hexane and diethyl ether (1:2) to afford the intermediate 2,3-dioleyloxyl(dimethylamino)propane as a colorless oil. Quaternization was carried out by condensation of methyl chloride (50 ml) into a Parr pressure apparatus cooled to −78° C. and containing this compound (10 g). The sealed vessel was heated behind a safety shield at 70° C. for 48 hr. After cooling to 0° C., the reaction vessel was opened, and the excess methyl chloride was allowed to evaporate under a stream of nitrogen in a well-ventilated hood. The crude residue was recrystallized from acetonitrile to afford DOTMA as an off-white solid, mp 35°–58° C.

A solution of 20 mg N-[1-(2,3-dioleyloxy)propyl]-N,N, Ntrimethylammonium chloride (DOTMA) in 1 ml chloroform is evaporated under nitrogen until dry and dried overnight in a vacuum. The residue is resuspended in 2 ml redistilled $H_2O$ and ultrasonicated at 4° C. until the solution is clear. The solution is diluted with Hepes buffered saline (HBS) to a concentration of 1 mg/ml and filtered sterile through a 0.2 μm filter.

EXAMPLE 2

Transfer of digoxigenin-11-dUTP into adherent cells a) Fluorescence detection 1) Preparation of Digoxigenin-O-succinyl-ε-amidocaproic acid $C_{33}H_{49}O_9N$ M.W.: 603.8

In a 250 ml round-bottomed flask, 5 g digoxigenin-O-succinyl-N-hydroxysuccinimide ester (8.5 mMol) are dissolved in 150 ml dimethylformamide (DMF) and a suspension of 1.12 g 6-aminocaproic acid (8.5 mMol) and 1.2 ml triethylamine in 20 ml DMF added thereto. One stirs magnetically overnight, whereby a homogeneous solution gradually results. After this time, according to thin layer chromatography (silica gel; acetic acid ethyl ester/petroleum ether/ethanol 1:1:1, detection: spraying with a mixture of 10 ml glacial acetic acid+0.2 ml conc. $H_2SO_4$+0.1 ml anisaldehyde and heating to 120° C. up to the appearance of blue-black spots; $R_f$ about 0.7; $R_f$ digoxigenin-OSu ester about 0.85), the reaction is practically complete.

One completely distills off DMF in high vacuum and dissolves the remaining oil in 50 ml $H_2O$ with the addition of conc. ammonia solution. Then, by addition of 225 ml aqueous citric acid solution (100 g citric acid/l), the "free" digoxigeninamidocaproic acid is separated out. The resinous-viscous mass becomes solid by trituration with water; one filters off with suction, after washing several times with $H_2O$ and finally drying over $P_2O_5$ in oil pump vacuum.

Yield: 3.45 g=68% of theory

2) Preparation of Dioxigenin-O-succinyl-ε-amidocaproic acid-N-hydroxysuccinimide ester $C_{37}H_{52}O_{11}N_2$ M.W.: 700.8

In a 100 ml round-bottomed flask, 3.45 g digoxigenin-O-succinyl-ε-amidocaproic acid (5.7 mMol) are dissolved in 20 ml anhydrous dimethylformamide (DMF) and successively mixed with 0.7 g N-hydroxysuccinimide (6 mMol), as well as 1.3 g dicyclohexylcarbodiimide (6.3 mMol). One stirs overnight at room temperature, filters off with suction the next day from separated dicyclohexylurea and strips off the DMF in oil pump vacuum. The oil remaining behind is taken up in 20 ml acetic acid ethyl ester and stirred into about 150 ml ice-cold (−20° C.) petroleum ether. The precipitated initially still resinous-viscous product is triturated several times with ice-cold dry petroleum ether until solidification. After drying over $P_2O_5$ in a vacuum, one obtained 3.35 g=84% of theory Elementary analysis:

C calc: 63.4% H Calc: 7.5% N calc: 4.0%

C found: 63.1% H found: 7.7% N found: 4.07%

3) Preparation of Digoxigenin-11-dUTP (digoxigenin-O-succinyl-ε-amidocaproyl-[5-(amidoallyl)- 2'-desoxyuridine-5'-triphosphate]tetrasodium salt)

Digoxigenin-11-dUTP may be prepared according to the following protocol.

$C_{45}H_{63}O_{22}N_4P_3Na_4$ M.W.: 1196.7

260 mg digoxigenin-O-succinyl-ε-amidocaproic acid N-hydroxysuccinimide ester (0.37 mMol) are dissolved in 7 ml. DMF (anhydrous dimethylformamide) and added to a solution of 200 mg. 5-allylamino-2'-desoxyuridine-5'-triphosphate tetralithium salt (0.37 mMol) contained in 6 ml $H_2O$. To the mixture, one adds 62 ml of a 0.1 M sodium borate buffer having a pH 8.5, and is allowed to stir overnight at room temperature (about 15 hours).

After this time, in the paper electrophoresis (0.05 M citrate buffer, pH 5.0), one observes in UV light, besides some unreacted allylamino-dUTP, a somewhat deeper running spot of the desired compound (alternative: thin layer chromatography (TLC) on silica gel, elution agent isobutyric acid/concentrated ammonia solution/$H_2O$=66:1:33, detection in UV or spraying with anisaldehyde reagent— (mixture of 10 ml glacial acetic acid and 0.2 ml conc. $H_2SO_4$ and 0.1 ml anisaldehyde)—$R_f$ values: 5-allylamino-dUTP 0.45; Dig-amidocaproic acid OSu ester 0.7; Dig-11-dUTP 0.45).

For the purification, the reaction mixture is evaporated to the solid residue in oil pump vacuum, taken up in 200 ml H$_2$O and applied to an ion exchange column (DEAE-Sephadex A25, HCO$_3$—form, column dimensions 1.5×30 cm). After application, it is briefly washed with water, then eluted with a gradient of, in each case, 1 l H$_2$O to 0.4 M TEAB (triethylammonium bicarbonate), pH 8. The fractions containing the pure product are combined, concentrated in a vacuum and freed from excess TEAB by repeated evaporation with methanol (no more odor of free triethylamine). One takes up the flask content in a few ml water, passes the solution over a short cationic exchanger column DOWEX 50 WS8 (1–10 cm) in the Na$^+$form, washes the column until wash water (efficient) used to wash the column is nearly free of UV absorbing materials (measurement in UV at 240 nm) and evaporated in a vacuum to about 20 ml. After lyophilization, there are obtained 200 mg (45% of theory) Dig-11-dUTP-Na$_4$ as white powder.

Analysis: H$_2$O determination: 7.9%
Elementary analysis: (having regard to the H$_2$O content): C calc: 41.8% H calc: 5.3% N calc.: 4.3% P calc.: 7.2% C found: 41.08% H found: 5.35% N found: 4.7% P found: 7.1% UV Spectrum (phosphate buffer pH 7.0): maxima 220 nm, 290 nm.

10 µl digoxigenin-11-dUTP (preparation according to DE 38 13 278; 10 mg/ml in HBS) is added to 20 µl of a solution of liposomes prepared according to Example 1 and mixed. This mixture is added to growing cells (CHO cells, ATCC: CCL 61) adherent on integrated chamber slides (Miles) (medium: cell culture medium DMEM, Boehringer Mannheim GmbH, 500 µl with 10% foetal calf serum) and incubated in an incubator (37° C., 5% CO$_2$) for 2 hours. The supernatant is aspirated and the cells are washed 3 times with phosphate buffered saline, NaCl, 137 mmol/l; KCl, 2.7 mmol/l; Na$_2$HPO$_4$, 8 mmol/l; KH$_2$PO$_4$, 1.5 mmol/l; pH 7.5; (PBS) (37° C.) at room temperature for 2 min in each case. After the last aspiration the cells are fixed at −20° C. for 10 min with 100% methanol, −20° C. The methanol is aspirated and the cells are washed 3 times with PBS as described above. After the last aspiration they are incubated for 30 min with pure FCS. Subsequently the FCS is aspirated and they are washed 3 times, the Fab fragments of a polyclonal antibody directed towards digoxigenin which are conjugated with 5(6)-carboxy-X-rhodamine (Boehringer Mannheim) are added and incubated for 1 h at 37° C. Then they are washed 3 times with PBS as described above. After the last aspiration the wet slides are embedded in mounting medium such as e.g. Mowiol® (Höchst Company) and dried for 1 h at room temperature in darkness. A red fluorescence is visible in the fluorescence microscope with green excitation (572 nm).

b) Enzyme detection

5 µl digoxigenin-11-dUTP (10 mg/ml in HBS) is added to 10 µl of a solution of liposomes prepared according to Example 1 and mixed. This mixture is added to growing cells (CHO cells, ATCC: CCL 61) adherent in microliter plates (Nunc Company) (medium: cell culture medium DMEM, Boehringer Mannheim GmbH, 500 µl with 10% foetal calf serum) and incubated in an incubator (37° C., 5% CO$_2$) for 2 hours. The supernatant is aspirated and the cells are washed 3 times at room temperature for 2 min in each case with Tris buffered saline: Tris HCl, 50 mmol/l; NaCl, 150 mmol/l; pH 7.5; (TBS), (37° C.). After the last aspiration the cells are fixed at −20° C. for 10 min with 100% methanol at −20° C. The methanol is aspirated and the cells are washed 3 times with TBS as described above. After the last aspiration they are incubated for 30 min with pure FCS. Subsequently the FCS is aspirated and they are washed 3 times with TBS as described above. After the last aspiration the Fab fragments of a polyclonal antibody directed towards digoxigenin which are conjugated with alkaline phosphatase (AP) are added and incubated for 1 h at 37° C. They are then washed 3 times with TBS as described above. After the last aspiration the bound AP is detected with the substrate p-nitrophenylphosphate in a microtitre plate reader (SLT Company) at 405 nm.

EXAMPLE 3

Transfer of digoxigenin-11-UTP into adherent cells a)

The procedure is as in Example 2a) whereby digoxigenin-11-UTP (preparation analogous to DE 38 13 278) is used instead of digoxigenin-11-dUTP. A red fluorescence of the complete cell is visible in the fluorescence microscope with green excitation (572 nm).

b)

The procedure is as in Example 2b) whereby digoxigenin-11-UTP is used instead of digoxigenin-11-dUTP.

EXAMPLE 4

Transfer of digoxigenin-labelled DNA into adherent cells a)

The procedure is as in Example 2a) whereby 10 µl digoxigenin-labelled DNA (100 µg/ml, pBR 328) (preparation analogous to DE 38 13 278) is used instead of digoxigenin-11-dUTP. A red fluorescence of the complete cell is visible in the fluorescence microscope with green excitation (572 nm).

b)

The procedure is as in Example 2b) whereby 10 µl digoxigenin-labelled DNA (100 µg/ml, pBR 328) is used instead of digoxigenin-11-dUTP (preparation analogous to De 38 13 278).

EXAMPLE 5

Transfer of digoxigenin-labelled RNA into adherent cells a)

The procedure is as in Example 2a) whereby 10 µl digoxigenin-labelled RNA (100 µg/ml) such as e.g. the transcript of the neomycin gene (preparation analogous to DE 38 13 278) is used instead of digoxigenin-11-dUTP. A red fluorescence of the complete cell is visible in the fluorescence microscope with green excitation (572 nm).

b)

The procedure is as in Example 2a) whereby 10 µl digoxigenin-labelled RNA (100 µg/ml) such as e.g. the transcript of the neomycin gene (preparation analogous to DE 38 13 278) is used instead of digoxigenin-11-dUTP.

EXAMPLE 6

Preparation of fluorescein-dUTP a) 5(6)-carboxyfluorescein-ε-amidocaproyl-[5-(amidoallyl)-2'-deoxyuridine-5'-triphosphate] -tetralithium salt (fluorescein-dUTP)

586 mg 5(6)-carboxyfluorescein-e-amidocaproic acid-N-hydroxysuccinimide ester (1 mmol) (prepared in a two-step synthesis by reaction of 5(6)-carboxyfluorescein-N-hydroxysuccinimide ester (FLUOS, Boehringer Mannheim 1055089) with 6-aminocaproic acid and subsequent preparation of the N-hydroxysuccinimide ester) is dissolved in 20 μl dimethylformamide (DMF) and added to a solution of 547 mg 5-aminoallyl-2'-deoxyuridine-5'-triphosphate-tetralithium salt (1 mmol) in 20 ml 0.1 mol/l sodium borate buffer, pH 8.5. The mixture is stirred at room temperature overnight (ca 15 h) after which a nearly quantitative conversion into the desired product is observed by paper electrophoresis (0.05 mol/l citrate buffer, pH 5.0).

The reaction mixture is evaporated in a vacuum, the residue is taken up in 250 ml distilled water and loaded onto a DEAE Sephadex A-25 column (2×40 cm) in the chloride form for the ion-exchange chromatography. It is eluted with a linear gradient of water to 0.3 mol/l LiCl, the fractions containing the product are combined and concentrated to a total volume of ca 50 ml in a vacuum. This concentrate is added dropwise to 500 ml of a mixture of acetone/ethanol with vigorous stirring, whereby the nucleotide precipitates. The precipitate is centrifuged off and washed several times with acetone/ethanol 3:1 until it is free of chloride. After drying in a vacuum over $P_2O_5$/KOH 453 mg (45% of the theoretical yield) of the title compound are obtained in the form of a yellow powder.

Elementary analysis for $C_{39}H_{37}O_{24}N_4P_3Li_4$:

| — | | | |
|---|---|---|---|
| $C_{calc}$ | 43.9% | $C_{found}$ | 43.5% |
| $H_{calc}$ | 3.5% | $H_{found}$ | 3.65% |
| $N_{calc}$ | 5.25% | $N_{found}$ | 5.0% |
| $P_{calc}$ | 8.7% | $P_{found}$ | 8.9% |

$^{31}$P-NMR (D$_2$O): δ=−5.2 (d, $P_δ$), −10.3 (d, $P_α$), −21.3 (*t, $P_β$)

b) 5(6)-carboxyfluorescein-ε-amidocaproyl-[5-(amidoallyl)-uridine-5'-triphosphate]-tetralithium salt 586 mg 5(6)-carboxyfluorescein-ε-amidocaproic acid-N-hydroxysuccinimide ester (1 mmol) are reacted with 563 mg 5-aminoallyl-uridine-5'-triphosphate tetralithium salt (1 mmol) in DMF/0.1 mol/l sodium borate buffer pH 8.5 analogous to Example 6a).

The reaction mixture is likewise processed in the manner described in Example 6a) after which 520 mg (50% of the theoretical yield) of the desired compound is obtained as a yellow/orange amorphic powder.

Elementary analysis for $C_{39}H_{37}O_{15}N_4P_3Li_4$:

| $C_{ber}$ | 43,3% | $C_{gef}$ | 42,9% |
|---|---|---|---|
| $H_{ber}$ | 3,4% | $H_{gef}$ | 3,5% |
| $N_{ber}$ | 5,2% | $N_{gef}$ | 5,1% |
| $P_{ber}$ | 8,6% | $P_{gef}$ | 8,75% |

The 31P-NMR spectrum is identical with that of the corresponding 2'-deoxy derivative.

EXAMPLE 7

Transfer of fluorescein-dUTP into adherent cells a)

10 μl fluorescein-dUTP (Example 6a) is added to 20 μl of a solution of liposomes (1 mg/ml) prepared according to Example 1 and mixed. This mixture is added to growing cells (CHO cells, ATCC: CCL 61) adherent on integrated chamber slides (Miles) (medium: cell culture medium DMEM, Boehringer Mannheim GmbH, 500 μl with 10% foetal calf serum) and incubated in an incubator (37° C., 5% $CO_2$) for 2 hours. The supernatant is aspirated and the cells are washed 3 times with (PBS), (37° C.) at room temperature for 2 min in each case. After the last aspiration the cells are fixed at −20° C. for 10 min with 100% methanol, −20° C. The methanol is aspirated and the cells are washed 3 times with PBS as described above. After the last aspiration the wet slides are embedded in mounting medium such as e.g. Mowiol® (Hëchst Company) and dried at room temperature in darkness. A green fluorescence of the cell nuclei is visible in the fluorescence microscope with blue excitation (494 nm).

The fluorescence-labelled cells can also be analyzed in a FACS (fluorescence activated cell sorter). The fixation with methanol can be omitted for this application.

b)

10 μl fluorescein-dUTP is added to 20 μl of a solution of liposomes (1 mg/ml) prepared according to Example 1 and mixed. This mixture is added to growing cells (CHO cells) adherent on microtitre plates (Nunc Company) (medium: cell culture medium DMEM, Boehringer Mannheim GmbH, 500 μl with 10% foetal calf serum) and incubated in an incubator (37° C., 5% $CO_2$) for 2 hours. The supernatant is aspirated and the cells are washed 3 times with (PBS) (37° C.) at room temperature for 2 min in each case. After the last aspiration the cells are fixed at −20° C. for 10 min with 100% methanol, −20° C. The methanol is aspirated and the cells are washed 3 times with PBS as described above. The detection is carried out in a fluorescence photometer (Flow Company). The fluorescence-labelled cells can also be analyzed according to known methods in a FACS (fluorescence activated cell sorter). The fixation with methanol can be omitted for this application.

EXAMPLE 8

Transfer of digoxigenin-11-dUTP into cells in suspension a) Fluorescence detection 10 μl digoxigenin-11-dUTP (10 mg/ml in HBS) is added to 20 μl of a solution of liposomes (1 mg/ml) prepared according to Example 1 and mixed. This mixture is added to cells growing in suspension (NS-1, ATCC: TIB 18) in integrated chamber slides (Miles) (medium: cell culture medium DMEM, Boehringer Mannheim GmbH, 500 μl with 10% foetal calf serum) and incubated in an incubator (37° C., 5% $CO_2$) for 2 hours. Before aspirating the supernatant the cells are centrifuged down to the bottom of the slide (Zytospinzentrifuge, Shandon Company, 30 g) and then the supernatant is carefully aspirated. The cells are washed 3 times with PBS (37° C.) at room temperature for 2 min in each case. Before aspirating the washing buffer the cells have to be centrifuged down to the bottom of the slide as described above. After the last aspiration the cells are dried onto the slide at 37° C. for 1 h and then fixed with 100% methanol, −20° C. for 10 min at −20° C. The methanol is aspirated and the cells are washed 3 times with PBS as described above. After the last aspiration they are incubated with pure FCS for 30 min. Subsequently the FCS is aspirated and the cells are washed 3 times with PBS as described above. After the last aspiration the Fab fragments of a polyclonal antibody directed towards digoxigenin which are conjugated with 5(6)-carboxy-X-rhodamine are added and incubated for 1 h at 37° C. Then they are washed 3 times with PBS as described above. After the last aspiration the wet slides are embedded in mounting medium such as e.g. Mowiol® (Hëchst Company) and dried for 1 h at room temperature in darkness. A red fluorescence of the cell nuclei is visible in the fluorescence microscope with green excitation (572 nm).

b) Enzyme detection

5 μl digoxigenin-11-dUTP (10 mg/ml in HBS) is added to 10 μl of a solution of liposomes (1 mg/ml) prepared according to Example 1 and mixed. This mixture is added to cells growing in suspension (NS-1, ATCC: TIB 18) in microtitre plates (Nunc Company) (medium: cell culture medium DMEM, Boehringer Mannheim GmbH, 500 μl with 10% foetal calf serum) and incubated in an incubator (37° C., 5% $CO_2$) for 2 hours. Before aspirating the supernatant the cells are centrifuged down to the bottom of the microtitre plate (centrifuge with inserts for microtitre plates, Hettich Company, 200 g) and then the supernatant is carefully aspirated. The cells are washed 3 times with TBS (37° C.) at room temperature for 2 min in each case. Before aspirating the washing buffer the cells have to be centrifuged down each time to the bottom of the microtitre plate as described above. After the last aspiration the cells are dried onto the bottom of the microtitre plate at 37° C. for 1 h and then fixed with 100% methanol, −20° C. for 10 min at −20° C. The methanol is aspirated and the cells are washed 3 times with TBS as described above. After the last aspiration they are incubated with pure FCS for 30 min at 37° C. Subsequently the FCS is aspirated and the cells are washed 3 times with TBS as described above. After the last aspiration the Fab fragments of a polyclonal antibody directed towards digoxigenin which are conjugated with alkaline phosphatase (AP) are added and incubated for 1 h at 37° C. Then they are washed 3 times with TBS as described above. After the last aspiration the bound AP is detected in a microtitre plate reader (SLT Company) with the substrate p-nitrophenylphosphate at 405 nm.

EXAMPLE 9

Transfer of digoxigenin-11-UTP into cells in suspension a)

The procedure is as in Example 7a) whereby digoxigenin-11-UTP is used instead of digoxigenin-11-dUTP. A red fluorescence of the complete cell is visible in the fluorescence microscope with green excitation (572 nm).

b)

The procedure is as in Example 7b) whereby digoxigenin-11-UTP is used instead of digoxigenin-11-dUTP.

EXAMPLE 10

Transfer of digoxigenin-labelled DNA into cells in suspension a)

The procedure is as in Example 7a) whereby 10 μl digoxigenin-labelled DNA (100 μg/ml, pBR 328) is used instead of digoxigenin-11-dUTP. A red fluorescence of the complete cell is visible in the fluorescence microscope with green excitation (572 nm).

b)

The procedure is as in Example 7b) whereby 10 μl digoxigenin-labelled DNA (100 μg/ml, pBR 328) is used instead of digoxigenin-11-dUTP

EXAMPLE 11

Transfer of digoxigenin-1abelled RNA into cells in suspension a)

The procedure is as in Example 7a) whereby 10 μl digoxigenin-labelled RNA (100 μg/ml), such as e.g. the transcript of the neomycin gene, is used instead of digoxigenin-11-dUTP. A red fluorescence of the complete cell is visible in the fluorescence microscope with green excitation (572 nm).

b)

The procedure is as in Example 7b) whereby 10 μl digoxigenin-labelled RNA (100 μg/ml), such as e.g. the transcript of the neomycin gene, is used instead of digoxigenin-11-dUTP.

EXAMPLE 12

Transfer of fluorescein-dUTP into cells in suspension a)

10 μl fluorescein-dUTP (10 mg/ml in HBS) is added to 20 μl of a solution of liposomes (1 mg/ml) prepared according to Example 1 and mixed. This mixture is added to cells growing in suspension (NS-1, ATCC: TIB 18) in integrated chamber slides (Miles) (medium: cell culture medium DMEM, Boehringer Mannheim GmbH, 500 μl with 10% foetal calf serum) and incubated in an incubator (37° C., 5% $CO_2$) for 2 hours. Before aspirating the supernatant the cells are centrifuged down to the bottom of the slide (Zytospinzentrifuge, Shandon Company, 30 g) and then the supernatant is carefully aspirated. The cells are washed 3 times with PBS (37° C.) at room temperature for 2 min in each case. Before aspirating the washing buffer the cells have to be centrifuged down each time to the bottom of the slide as described above. After the last aspiration the cells are dried onto the slide at 37° C. for 30 min and then fixed with 100% methanol, −20° C. for 10 min at −20° C. The methanol is aspirated and the cells are washed 3 times with PBS as described above. After the last aspiration the wet slides are embedded in mounting medium such as e.g. Mowiol® (Hëchst Company) and dried for 1 h at room temperature in darkness. A green fluorescence of the cell nuclei is visible in the fluorescence microscope with blue excitation (494 nm).

The fluorescence-labelled cells can also be analyzed in a FACS (fluorescence activated cell sorter). Using this application the fixation with methanol can be omitted.

b)

5 μl fluorescein-dUTP (10 mg/ml in HBS) is added to 10 μl of a solution of liposomes (1 mg/ml) prepared according to Example 1 and mixed. This mixture is added to cells growing in suspension (NS-1, ATCC: TIB 18) in microtitre plates (Nunc Company) (medium: cell culture medium DMEM, Boehringer Mannheim GmbH, 500 μl with 10% foetal calf serum) and incubated in an incubator (37° C., 5% $CO_2$) for 2 hours. Before aspirating the supernatant the cells are centrifuged down to the bottom of the microtitre plate (centrifuge with inserts for microtitre plates, Hettich Company, 200 g) and then the supernatant is carefully aspirated. The cells are washed 3 times with PBS (37° C.) at room temperature for 2 min in each case. Before aspirating the washing buffer the cells have to be centrifuged down each time to the bottom of the microtitre plate as described above. After the last aspiration the cells are dried onto the bottom of the microtitre plate at 37° C. for 1 h and then fixed with 100% methanol, −20° C. for 10 min at −20° C. The methanol is aspirated and the cells are washed 3 times with PBS as described above. The detection is carried out in a fluorescence photometer (Flow Company).

The fluorescence-labelled cells can also be analyzed in a FACS (fluorescence activated cell sorter). The fixation with methanol can be omitted for this application.

EXAMPLE 13

Transfer of digoxigenin-11-dUTP into adherent cells analogous to the procedure in PNAS 84 (1987) 7413–7417

20 μl of a solution of liposomes (1 mg/ml) prepared according to Example 1 is diluted with HBS to 250 μl. 10 μl digoxigenin-11-dUTP (10 mg/ml) is diluted with HBS to 250 μl. Both solutions are mixed and applied onto cells (CHO), which have previously been washed with HBS in order to remove residual serum, and incubated for 2 h in an incubator (37° C., 5% $CO_2$). The procedure is then according to Example 2. Only a very slight fluorescence of the cell nuclei is visible in the fluorescence microscope with green excitation (572 nm).

EXAMPLE 14

Preparation of liposomes containing labelled nucleotide 50 mg 1,2-dioleyl-sn-glycero-3-phosphorylcholine are dissolved in 5 ml chloroform and the solvent is drawn off in a rotary evaporator at a water bath temperature of 30° C. Subsequently 5 mg digoxigenin-labelled dUTP dissolved in 25 ml re-distilled water is added and ultrasonicated continually for 10 min and filtered sterile through a 0.2 μm filter.

EXAMPLE 15

Transfer of digoxigenin-11-dUTP into cells by means of liposomes prepared according to Example 14.

333 μl of the liposomes prepared according to Example 14 are added to 166 μl culture medium with serum (composition as in Example 2) and mixed. After aspirating the culture medium, 250 μl of the mixture is added to the cells when using microtitre plates and the whole mixture is added when using integrated chamber slides. After incubating for 2 h (37° C., 5% $CO_2$) the procedure is analogous to the other Examples.

We claim:

1. Method for the determination of the rate of nucleic acid synthesis in a eukaryotic cell, comprising introducing a nucleotide which is non-radioactively labelled or derivatized with a hapten into said cell with the addition of a cationic liposome which does not encapsulate said nucleotide and determining the rate of nucleic acid synthesis by determining incorporation of the non-radioactively labelled or derivatized nucleotide into nucleic acids of said eukaryotic cell as a function of time.

2. Method as in claim 1, wherein said nucleotide is derivatized with a hapten which is a first member of a binding pair and said method further comprises determining the rate of nucleic acid synthesis by adding a labelled, second member of the binding pair which binds to said first member in said eukaryotic cell and determining binding between said first and second member.

3. Method as in claim 2, wherein said second member of said binding pair is a labelled anti-hapten antibody.

4. Method as in claim 1 wherein said nucleotide is a pyrimidine nucleotide which has been labelled or derivatized at the 5-position or a purine nucleotide labelled or derivatized at the 8-position, or a 7-deaza purine nucleotide labelled or derivatized at the 7-position, said nucleotide having as a sugar residue a ribose, deoxyribose or dideoxyribose unit.

5. Method as in claim 4, wherein said nucleotide is 5-digoxigenin-2-'-deoxyuridine triphosphate.

6. Method as in claim 2 wherein said second member of said binding pair is labelled with an enzyme and said method further comprises adding a substrate for said enzyme to said eukaryotic cell and determining cleavage of said substrate.

7. Method as in claim 6, wherein said enzyme is β-galactosidase, alkaline phosphatase or peroxidase.

8. Method as in claim 1 further comprising culturing the eukaryotic cells in a cell culture medium having serum added to said culture medium with the introduction of the cationic liposomes and said labelled or derivatized nucleotide.

9. Method as claimed in claim 1, further comprising determining said rate of nucleic acid synthesis by immunocytochemical examination of proliferating cells.

10. Method as in claim 1, further comprising determining said rate of nucleic acid synthesis via an enzyme linked immunosorbent assay.

11. Method of claim 1, wherein said cationic liposome comprises N-[1(2,3-dioleyloxy)propyl]-N,N,N-trimethylammonium chloride.

12. Method of claim 2, wherein said second member of said binding pair is labelled with a fluorescent dye or a luminescent dye.

13. Method of claim 12, wherein said fluorescent dye is resorufin, fluorescein, coumarin or rhodamine.

14. Method of claim 3, wherein said labelled anti-hapten antibody is labelled with a fluorescent dye or a luminescent dye.

15. Method of claim 6, wherein said second member of said binding pair is a labelled, anti-hapten antibody and said nucleotide is derivatized by a hapten.

16. Method for the determination of the rate of nucleic acid synthesis in a eukaryotic cell, comprising introducing a nucleotide which is derivatized with a hapten selected from the group consisting of digoxigenin, biotin and fluorescein into said cell with the addition of a cationic liposome which does not encapsulate said nucleotide and determining the rate of nucleic acid synthesis be determining incorporation of the derivatized nucleotide into nucleic acids of said eukaryotic cell as a function of time.

17. Method for the determination of the rate of nucleic acid synthesis in a eukaryotic cell, comprising introducing a nucleotide which has been non-radioactively labelled with a fluorescent dye or a luminescent dye into said cell with the addition of a cationic liposome which does not encapsulate said nucleotide and determining the rate of nucleic acid synthesis by determining incorporation of the non-radioactively labelled nucleotide into nucleic acids of said eukaryotic cell as a function of time.

18. Method as in claim 17 further comprising determining said rate of nucleic acid synthesis by measuring immunofluorescence of proliferating cells in an immunofluorescence assay.

* * * * *